(12) United States Patent
Tokarski et al.

(10) Patent No.: US 11,608,521 B2
(45) Date of Patent: *Mar. 21, 2023

(54) METHOD OF DETECTING GENETIC MATERIAL IN A BIOLOGICAL SAMPLE AND A DEVICE FOR ITS IMPLEMENTATION

(71) Applicant: Genomtec S.A., Wroclaw (PL)

(72) Inventors: Miron Tokarski, Brzeg (PL); Henryk Waldemar Roguszczak, Wroclaw (PL)

(73) Assignee: Genomtec S.A., Wroclaw (PL)

( * ) Notice: Subject to any disclaimer, the term of this patent is extended or adjusted under 35 U.S.C. 154(b) by 306 days.

This patent is subject to a terminal disclaimer.

(21) Appl. No.: 17/002,321

(22) Filed: Aug. 25, 2020

(65) Prior Publication Data

US 2021/0040549 A1 Feb. 11, 2021

Related U.S. Application Data

(63) Continuation of application No. 15/850,733, filed on Dec. 21, 2017, now Pat. No. 10,781,479.

(30) Foreign Application Priority Data

Dec. 21, 2016 (PL) .......................................... 419907

(51) Int. Cl.
*C12Q 1/6844* (2018.01)
*C12Q 1/6816* (2018.01)
(Continued)

(52) U.S. Cl.
CPC ............ *C12Q 1/6844* (2013.01); *B01L 3/502* (2013.01); *B01L 3/502738* (2013.01); *B01L 7/52* (2013.01);
(Continued)

(58) Field of Classification Search
CPC ................... C12Q 1/6844; B01L 3/502; B01L 2400/0406; B01L 2400/0487; G01N 21/6428
See application file for complete search history.

(56) References Cited

U.S. PATENT DOCUMENTS

2009/0061450 A1 3/2009 Hunter
2011/0312703 A1* 12/2011 Facer .................... B01L 3/5027
435/303.1
(Continued)

FOREIGN PATENT DOCUMENTS

WO 2011/106384 A1 9/2011
WO 2011/156841 A1 12/2011
(Continued)

OTHER PUBLICATIONS

Invitrogen brochure "SYBR Green I Nucleic Acid Gel Stain", pp. 1-6 (Year: 2006).*
(Continued)

*Primary Examiner* — Teresa E Strzelecka
(74) *Attorney, Agent, or Firm* — Arrigo, Lee, Guttman & Mouta-Bellum LLP

(57) ABSTRACT

The object of the invention is a method of detecting genetic material in a biological sample in which the biological sample is loaded into the reaction cartridge (6) and then the reaction cartridge (6) is placed in the control device, the collected biological sample is taken to the isolation chamber (7), isolation of biological material from the tested sample by heating the isolation chamber (7), the isolated genetic material is moved into a plurality of reaction chambers (8.1, 8.2, 8.3, 8.4), genetic material is amplified by heating the reaction chambers (8.1, 8.2, 8.3, 8.4), lyophilized reagents for genetic material amplification together with lyophilized fluorescent tag intercalating with genetic material are present in the reaction chambers (8.1, 8.2, 8.3, 8.4), and signal
(Continued)

detection from fluorescent tags is carried out along with the genetic material amplification stage.

16 Claims, 7 Drawing Sheets

(51) Int. Cl.
  *G01N 21/64* (2006.01)
  *B01L 7/00* (2006.01)
  *B01L 3/00* (2006.01)
  *C12Q 1/689* (2018.01)
  *C12Q 1/6895* (2018.01)
  *C12Q 1/70* (2006.01)

(52) U.S. Cl.
  CPC ........... *C12Q 1/689* (2013.01); *C12Q 1/6816* (2013.01); *C12Q 1/6895* (2013.01); *C12Q 1/703* (2013.01); *G01N 21/6428* (2013.01); *B01L 2200/0605* (2013.01); *B01L 2300/0663* (2013.01); *B01L 2300/0672* (2013.01); *B01L 2300/0816* (2013.01); *B01L 2300/165* (2013.01); *B01L 2300/1872* (2013.01); *B01L 2400/0406* (2013.01); *B01L 2400/0487* (2013.01); *B01L 2400/06* (2013.01); *G01N 2021/6439* (2013.01); *G01N 2201/062* (2013.01)

(56) References Cited

U.S. PATENT DOCUMENTS

| | | | |
|---|---|---|---|
| 2017/0113221 A1* | 4/2017 | Hoffman | B01L 3/527 |
| 2019/0032114 A1* | 1/2019 | Trivedi | B01L 3/5027 |

FOREIGN PATENT DOCUMENTS

| | | |
|---|---|---|
| WO | 2016/004539 A1 | 1/2016 |
| WO | 2016/115542 A1 | 7/2016 |
| WO | 2016/172724 A1 | 10/2016 |
| WO | WO-2018071541 A1 * | 4/2018 ............ B01L 3/5027 |

OTHER PUBLICATIONS

Extended European Search Report, Application No. 17002043-1118, dated Mar. 15, 2018.

Michael G. Mauk, et al., "Integrated Microfluidic Nucleic Acid Isolation, Isothermal Amplification, and Amplicon Quantification," Microarrays 2015, 4, 474-489.

Song J, Liu C, Bais S, Mauk MG, Bau HH, Greenberg RM (2015) Molecular Detection of Schistosome Infections with a Disposable Microfluidic Cassette. PLoS Negl Trop Dis 9(12): e0004318. doi:10.1371/journal.pntd.0004318.

* cited by examiner

A)

B)

C)

D)

METHOD OF DETECTING GENETIC MATERIAL IN A BIOLOGICAL SAMPLE AND A DEVICE FOR ITS IMPLEMENTATION

The object of the invention is a method of detecting genetic material (including DNA and RNA) in a biological material sample, in particular using LAMP technology (Loop-mediated Isothermal AMPlification) for amplifying genetic material and the device for its implementation. The object of the invention is used for rapid and mobile detection of bacterial, viral and fungal pathogens in the biological material obtained.

Currently there is a demand for rapid, inexpensive and effective diagnostic methods to identify bacterial, viral and fungal pathogens that may be microbial contaminants, e.g. of food products.

The US patent application US2009061450A1 discloses a device for diagnosis and assay of respiratory pathogens, comprising a nasal sampling device, a single entry, disposable microfluidic cartridge for target nucleic acid amplification, and an instrument with on-board assay control platform and target detection means. A device for sampling is a sample carrier being placed in an appropriate receptacle in a microfluidic cartridge so that they are fluidly connected to each other. A number of chambers may be distinguished in the microfluidic cartridge, where subsequent steps of pathogen assay method are performed, wherein first stage includes isolation of genetic material from the tested sample, the isolated material is then amplified and subjected to detection. In one embodiment of cited solution, amplification of genetic material is accomplished using the LAMP method. In the reaction chamber, where amplification takes place, it is necessary to provide a set and stable temperature, which in presented solution is achieved by the ITO heating element printed on a microfluidic device. Fluorescent tag intercalating with genetic material is added after performing genetic material amplification, allowing optical detection in real time.

In turn, US patent application US2012264132A1 discloses a device and method of processing of samples, including essentially isothermal amplification of nucleic acids. The device according to a cited invention comprises a first substrate having a first population areas, at least one area of the first population having at least one satellite area disposed proximate to the at least one area, and at least one satellite area being adapted to retain material from the first area. The device additionally comprises a second substrate having a second population area formed therein, the first and second substrates being engaged with one another such that the relative motion between the first and second substrates places at least some of the first population areas in alignment with at least some of the second population areas so that they are in fluid communication with one another. The device may be used for amplifying genetic material by contacting a sample material disposed in a plurality of first areas, the sample material comprising a nucleic acid target, and at least one of the first areas containing one molecule of the nucleic acid target, with a reactant material disposed in a plurality of second areas, the contacting being effected by pairwise placement of at least some of the first areas and at least some of the second areas into direct fluid communication with one another. The said contacting of the materials effects amplification of nucleic acid target molecule.

US patent application US20140335527A1 discloses a system and method for mobile analysis of nucleic acids and proteins. Mobile analysis system is a small wireless device, which communicates with the used via the display and keyboard. Mobile analysis system is using connected modules for extracting, amplifying and detecting nucleic acids from the samples. The entire process, together with data processing takes usually not more than 20 minutes. In the first stage of the analysis method of genetic material the biological sample is loaded onto an integrated chip. The loading of the biological sample can be accomplished manually, through sample inlet port or through an automated sampling. In the integrated chip the sample is transported to an extraction module in which the process of extracting genetic material from the biological sample is performed. The isolated nucleic acids are then transported to the amplification module, in which in one embodiment amplification is performed using LAMP method. The extraction and amplification methods contain all the reagents needed to carry them out. Amplification requires retaining set increased temperature, which can be achieved through infrared heating elements. Amplified genetic material goes to the detection module in which it is detected, for example, by a fluorescent signal derived from appropriate tags attached to the detected DNA. Therefore, one of the chambers of genetic material amplification may be preloaded with e.g. fluorescently tagged LAMP master mix. The entire integrated chip is transparent, allowing transmission of light beams for heating the respective modules and detecting fluorescence signal.

A technical issue to be solved is providing a method of detecting genetic material (in particular DNA and/or RNA) in a biological material sample and the device for its implementation which will allow rapid detection of preferred pathogens, at the same time, the device will be simple to build, complete, mobile, relatively inexpensive to manufacture and will allow storage of reaction cartridges for extended periods of time and will not be associated with specific storage conditions such as very low temperatures. It is also preferred for the reaction cartridges, being a part of the device for detecting the pathogen in the biological material sample, to be suitable for disposal and the device itself to have limited energy consumption. Moreover, it is preferred that the developed method of pathogen detection reduces the number of steps required, making it simpler and faster to implement and that the construction of the device for its implementation provides a reduced risk of contamination of the biological material sample. The invention provides such a solution.

A first object of the invention is a method of detecting genetic material in a biological sample including the following stages:

a) the biological sample is loaded into the reaction cartridge and then or before that reaction cartridge is placed in the measurement device, b) the collected biological sample is taken to the isolation chamber, c) isolation of biological material from the tested sample by heating the isolation chamber, d) the isolated genetic material is moved into a plurality of reaction chambers, e) genetic material is amplified by heating the reaction chambers, characterized in that inside at least one of reaction chambers are present freeze-dried reagents for amplification of genetic material together with luminescent dye, comprising fluorescence dye or quantum-dots binding genetic material to be detected, whereas simultaneously with the stage of amplification of genetic material a detection of luminescent signal from luminescent markers is registered.

In preferred embodiment of the invention a biological sample is taken from a sampling system and stage a) is performed by loading the sampling system into to the reaction cartridge (6).

In another preferred embodiment of the invention heating of the isolation chamber and/or reaction chamber is performed through a plurality of heating units on LEDs with temperature detectors, preferably emitting electromagnetic radiation with a wavelength in the range of 350 nm to 530 nm.

In another preferred embodiment of the invention the heating unit of LEDs with temperature detectors comprises an optical temperature detector that detects electromagnetic radiation in the wavelength range of 4 μm to 12 μm.

In another preferred embodiment of the invention a biological sample is taken using capillary forces for the capillary in the sampling system.

Preferably lyophilized reagents for genetic material amplification include deoxynucleotides, specific primer sequences, reaction buffer, magnesium ions $Mg^{2+}$, preferably in the form of $MgSO_4$, polymerase capable of carrying out an amplification reaction, preferably Bst 3.0 polymerase.

Equally preferably, lyophilized fluorescent tag intercalating with detected genetic material is SYBR® GREEN.

For detection, according to the first and second aspect of the invention, the real-time detection of nucleic acid amplification product as well as the end-point technique oligonucleotides with a quantum dot molecule attached at the 5' end and a quencher attached at the 3'end. The sequence of the oligonucleotides used is complementary to the portion of the amplified region of the deoxyribonucleic acid fragment located between the designed primers F1 and B1c and for the portion of the amplified region of the nucleic acid fragment located between the designed primers F1c and B1. During the amplification reaction, a polymerase having a strand displacement activity and 5'>3' exonuclease activity is used, e.g. Bst DNA Polymerase, Full Length.

During the deoxyribonucleic acid amplification reaction, the probe binds to the complementary fragment in the amplified DNA segment. During the amplicon elongation, due to the exonuclease properties of the polymerase, the attached oligonucleotide is degraded, which results in separation of the quencher from the quantum dot. As a result of the separation of the quencher from the quantum dot, electromagnetic radiation is emitted in the UV, IR or VIS range after excitation of the quantum dot with the radiation wave-length specific for the material from which the quantum dot was created. The emitted signal is registered by a photosensitive element.

The use of quantum dots causes a significant reduction in the detection threshold due to the possibility of using a source of excitation light with a higher power, thanks to which it is possible to register the emission of electromagnetic radiation coming from a much smaller amount of released quantum dots. In addition, the use of quantum dots for marking oligonucleotide fragments allows for a better separation of excitation wavelength from the wavelength of emission signal in which detection of electromagnetic radiation occurs. What is more, quantum dots have an increased bleaching durability compared to traditional fluorochromes, which facilitates detection throughout the entire amplification reaction.

More preferably, the reaction cartridge comprises three reaction chambers, including a test chamber including specific primers for the genetic material tested, a positive control chamber that contains primers specific to a particular portion of the genetic material from which the biological material sample is derived and a negative control chamber, containing reaction components without primers.

In preferred embodiment of the invention the reaction chambers in a top view are circles, complementary and interconnected in the middle with a valve or a diaphragm.

In another preferred embodiment of the invention at stage c) the isolation chamber is heated to 95° C. from 5 minutes to 10 minutes.

In yet another preferred embodiment of the invention at stage e) the reaction chambers are heated to 65° C. from 15 minutes to 60 minutes.

Preferably stage b) is accomplished by means of a first pump, preferably in the form of a water tank closed with a diaphragm connected to a pressure-producing chamber or piston and bellows.

Equally preferably, step d) is accomplished by means of a second pump, preferably in the form of a hollow chamber closed with a diaphragm connected to a pressure-producing chamber.

More preferably, the method additionally comprises a stage of heating a reaction cartridge to temperatures above 100° C., preferably through a number of heating units on LEDs with temperature detectors.

A second object of the invention is a device for detecting genetic material in a biological sample, comprising a reaction cartridge and measurement device, the measurement device comprising a measurement chamber having a receptacle housing the reaction cartridge, wherein the reaction cartridge comprises an isolation chamber for isolating genetic material, which is connected with reaction chambers through the channels, for amplifying isolated genetic material. Freeze-dried reagents for amplification of genetic material together with luminescent dye, comprising fluorescence dye or quantum-dots binding genetic material to be detected, are present inside at least one of the reaction chambers. Simultaneously with the stage of amplification of the genetic material, the detection of luminescent signal from luminescent markers is registered.

In preferred embodiment of the invention the device comprises a detachable sampling system, the detachable sampling system comprising a plug and the reaction cartridge comprising a receptacle fitted to said plug and providing a stable and tight fluid connection between the sampling system and the reaction cartridge.

In another preferred embodiment of the invention the device additionally comprises a measurement module for image control and analysis, communication module, power supply module and display module.

In another preferred embodiment of the invention the measurement device comprises a plurality of heating units on LEDs with temperature detectors, preferably emitting electromagnetic radiation with a wavelength in the range of 350 nm to 530 nm, arranged substantially opposite the isolation chamber and reaction chambers such that the light beams emitted by said plurality of LEDs illuminate said isolation chamber and reaction chambers.

In another preferred embodiment of the invention the heating unit of LEDs with temperature detectors comprises an optical temperature detector that detects electromagnetic radiation in the wavelength range of 4 μm to 12 μm.

Preferably, the reaction chambers in a top view are circles, complementary and interconnected in the middle with a valve or a diaphragm.

Equally preferably, the sampling system comprises a capillary, to which a biological sample is taken, connected with a first pump, preferably in the form of a water tank closed with a diaphragm connected to a pressure-producing chamber or piston and bellows.

More preferably, lyophilized reagents for genetic material amplification include deoxynucleotides, specific primer sequences, reaction buffer, magnesium ions $Mg^{2+}$ (preferably in the form of $MgSO_4$), and polymerase capable of carrying out an amplification reaction (preferably Bst 3.0 polymerase).

In preferred embodiment of the invention, lyophilized fluorescent agent intercalating with detected genetic material is SYBR® GREEN.

In yet another preferred embodiment of the invention, the reaction cartridge comprises three reaction chambers, including a test chamber including specific primers for the genetic material tested, a positive control chamber that contains primers specific to a particular portion of the genetic material from which the biological material sample is derived and a negative control chamber, containing reaction components without primers.

In yet another preferred embodiment of the invention, the reaction cartridge comprises a second pump, preferably in the form of an empty chamber closed with a diaphragm connected to a pressure-producing chamber, causing the movement of isolated genetic material from the isolation chamber to the reaction chambers.

Preferably, the reaction cartridge and/or sampling system is made of a hydrophobic polymer and is a fully passive system.

Equally preferably, the isolation chamber and reaction chamber as well as the second pump in the reaction cartridge comprise the valves, preferably optical ones on the inlet and outlet channels, respectively.

More preferably, in the channel connecting the isolation chamber with the second pump there is a liquid detector, preferably a reflective infra-red one.

In preferred embodiment of the invention, liquid detectors, preferably reflective infra-red ones are located in outlet channels from the reaction chambers.

In another preferred embodiment of the invention, the measurement chamber has a controlled isothermal temperature in the range from 4° C. to 40° C., realized via a heating system, preferably in the form of a Peltier assembly.

In another preferred embodiment of the invention, the heating system comprises a connected fan and radiator, and an air-mixing wheel is located in the measurement chamber.

Preferably, the measurement chamber is insulated with thermal insulation.

Equally preferably, the device comprises a positioning mechanism of the reaction cartridge.

More preferably, the device comprises a pressure setting mechanism exerting a pressure on the pump in the reaction cartridge and an oppositely set pressure sensor.

In preferred embodiment of the invention, the device comprises additional UV LEDs illuminating the detection area.

In another preferred embodiment of the invention, the device comprises additional LEDs for operating liquid detectors and valves.

In another preferred embodiment of the invention, at the bottom of the isolation chamber and/or reaction chamber there is an absorption layer absorbing photon energy, preferably made of Cu or Al coated with oxides preferably, dyed black $Al_2O_3$.

A method of detecting genetic material in a biological sample according to the present invention allows to avoid the need to modify the biological material sample by placing it in the devices, reducing the probability of contamination and also allows the user to perform the test only by the end user. Moreover, no additional laboratory equipment or sterile reaction preparation conditions are required to complete the test. Additionally, lyophilization in the production process of the reaction components provides a significant increase in the usefulness of the reaction cartridge (even more than one year from the date of manufacture), and it is not necessary to store the reaction cartridge under refrigeration. Placing the primers, specific for the amplified nucleic acid fragment, inside the reaction chamber additionally reduces the susceptibility of the procedure to contamination, and further facilitates the study to the end user. In addition, placement of the dye in the reaction chamber enables immediate detection of the resulting reaction product without the end user taking action and significantly simplifies the entire detection process by reducing the number of steps required. The reaction cartridge, as well as the sampling system, are made, as fully passive components, from one polymer material, allowing them to be safely disposed of, benefiting the environment. In addition, LEDs for heating the isolation chamber and the reaction chambers used in the control device reduce the energy consumption of the whole process.

Exemplary embodiments of the invention are shown in figures of the drawing, in which FIG. 1, 6 shows a schematic representation of the sampling system and the reaction cartridge according to one embodiment of the present invention, FIG. 2, 7 shows the reaction cartridge according to another embodiment of the present invention, FIG. 3 shows the reaction cartridge according to yet another embodiment of the present invention, FIG. 4 shows various embodiments of the valves used in different embodiments of the reaction cartridge, while FIG. 5 shows a block diagram of the measurement device according to one embodiment of the present invention.

EXAMPLE 1

Figure 1:
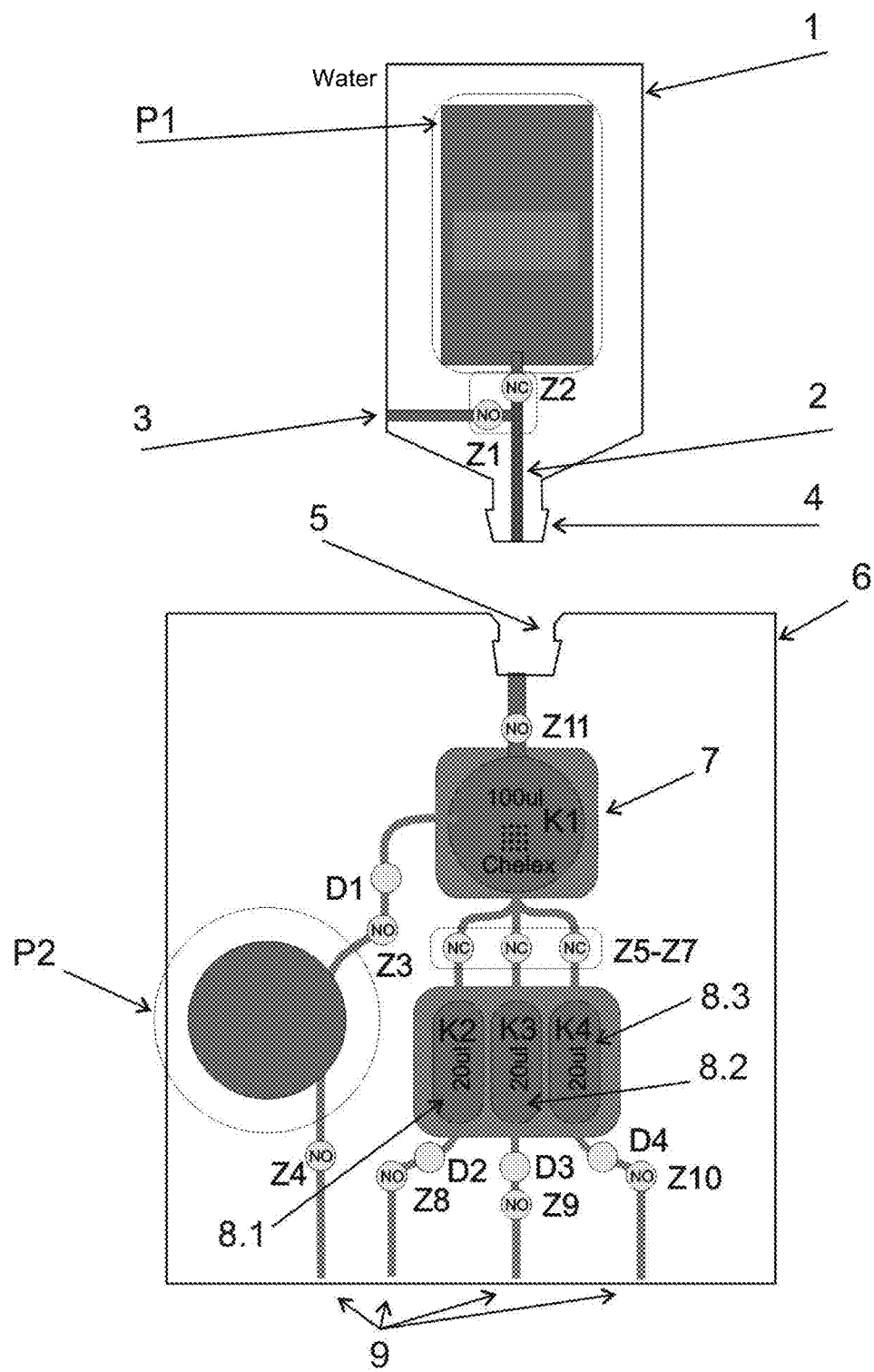
FIG. 1 shows a schematic representation of the sampling system and the reaction cartridge according to one embodiment of the present invention.
Figure 6:
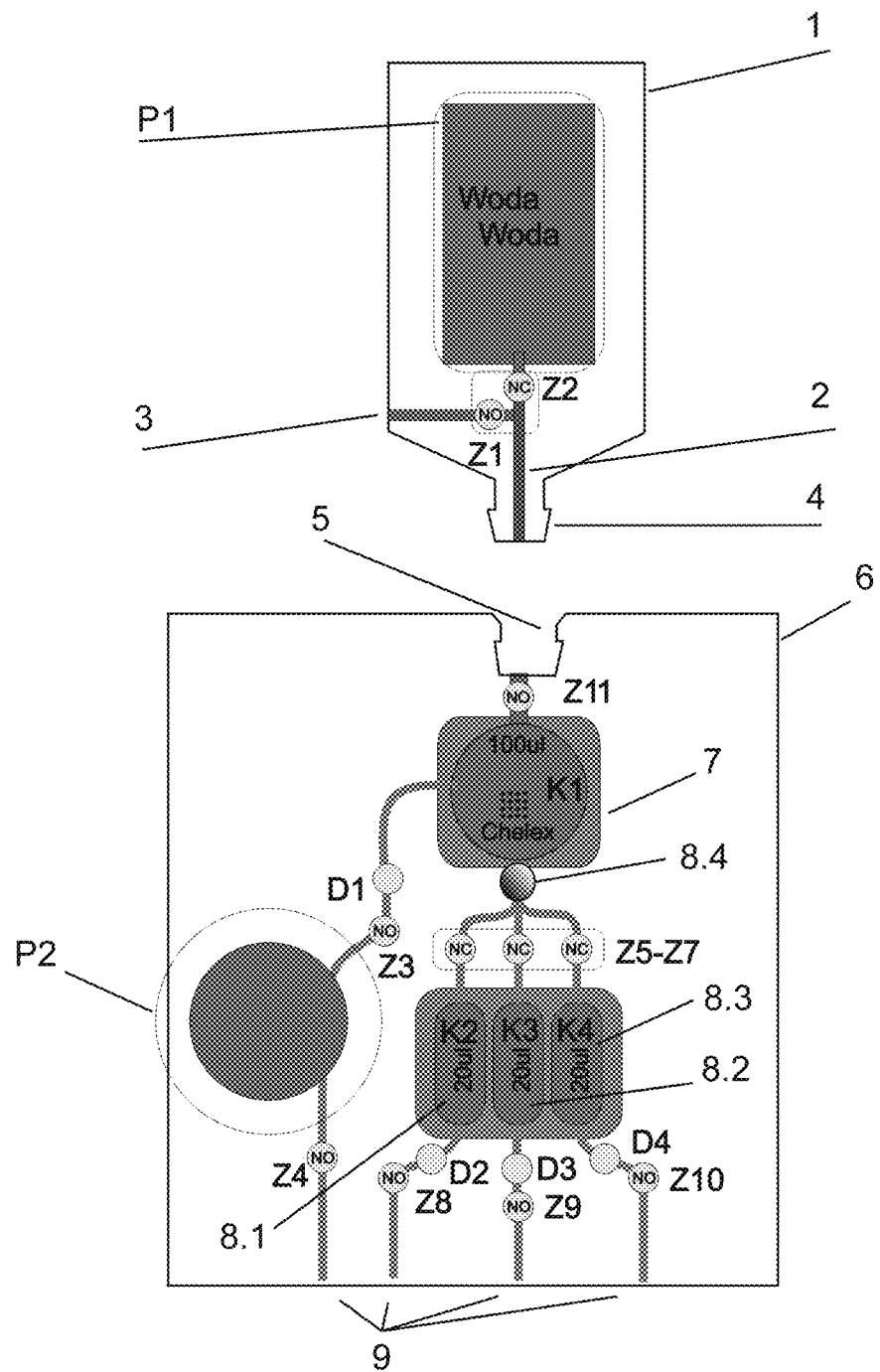
FIG. 6 shows a schematic representation of the sampling system and the reaction cartridge according to one embodiment of the present invention.
Figure 7:
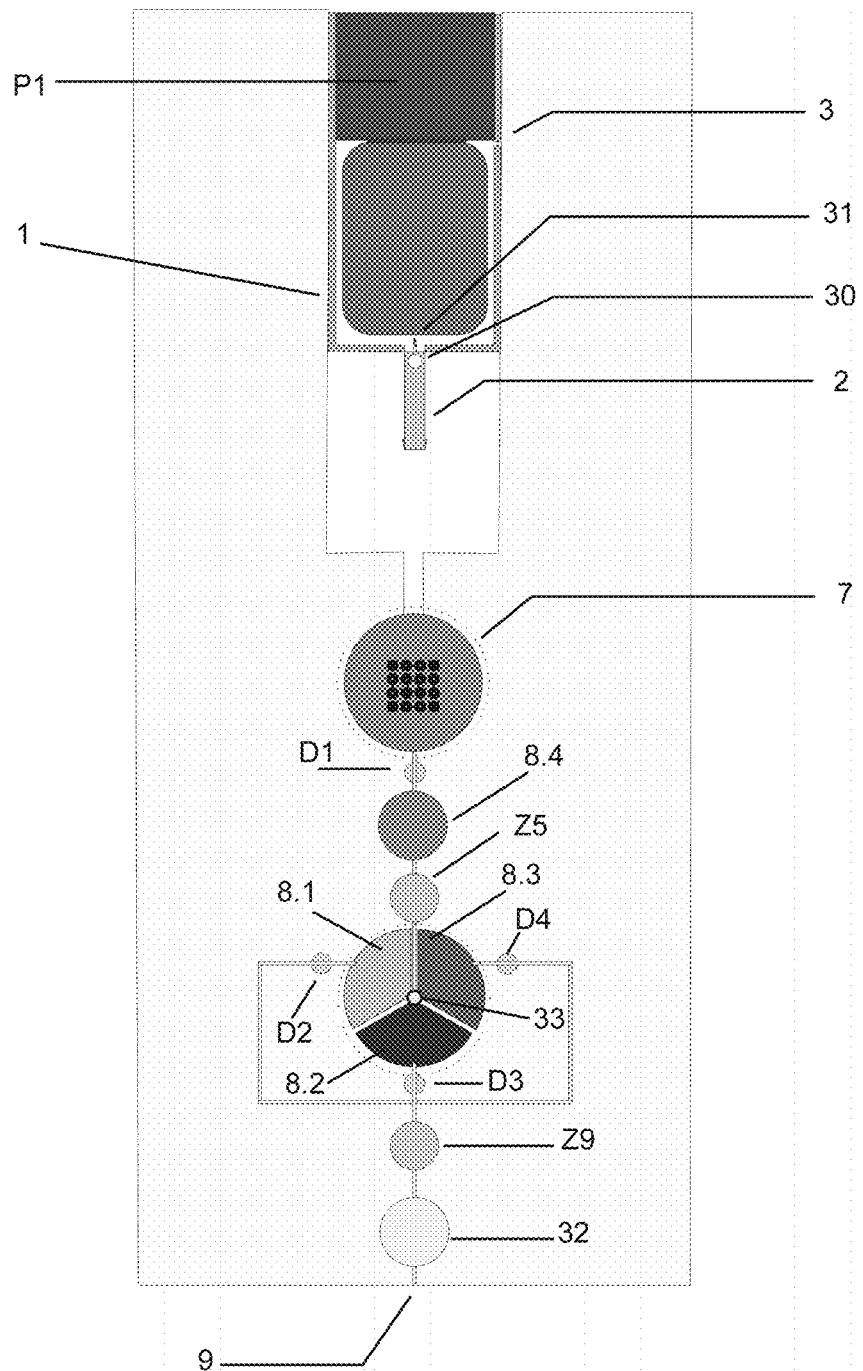
FIG. 7 shows the reaction cartridge according to another embodiment of the present invention.

A device for detecting genetic material in a biological sample according to embodiment of the present invention was partially illustrated schematically (without a measurement device) in FIG. 1 and its variety on FIG. 6. The biological material sample (e.g. capillary blood, whole blood, saliva, body cavity fluid) taken using the sampling system 1, is introduced into a reaction cartridge 6 made from a hydrophilic polymer coated with an anticoagulant layer, e.g. sodium citrate, EDTA, by capillary forces in a volume not exceeding 1 ml (in the embodiment shown in FIG. 1 the volume is 10 µl). The filling of the capillary 2, is signalled to the end user by means of a tag at the end of the channel (not shown), for example by observing the channel filling up to the control window or by means of a light and/or sound signal. The biological material is transported by the pressure of the fluid exiting the chamber containing water intended for molecular diagnostics.

The mixture of biological material and water passes from the capillary 2 into the isolation chamber 7 at its end. In the isolation chamber 7 there is a Chelex 100 immobilized ion exchange resin or other material capable of binding inhibitors of the amplification reaction of genetic material. After the mixture has passed through, the contents of the isolation chamber 7 is heated to 70° C. or higher for more than 5 minutes. At this time, there is a thermal lysis of the cells and, in some cases, also the viral nucleocapsides contained in the biological material, thus releasing the genetic material from their inside. Depending on the type of pathogen, the temperature can be increased to 98° C. At the end of the heating process, the mixture is cooled (passively or actively, e.g. by stream of air flowing through the fan) and moved to at least one reaction chamber 8.1, 8.2, 8.3, 8.4 at a volume of at least 0.1 µl (in the embodiment shown in FIGS. 1 and 6 reaction chambers 8.1, 8.2, 8.3 have a volume of 20 µl) in which a lyophilisate, containing the appropriate amounts of substances necessary to perform a specific isothermal amplification reaction and detection of the selected fragment of genetic material amplified during the reaction, is located. Lyophilization in the production process of the reaction components allows a significant increase in the usefulness of the reaction cartridge (even more than one year from the date of manufacture), and it is not necessary to store the reaction cartridge under refrigeration. The reaction chamber 8.1, 8.2, 8.3 houses also a lyophilized dye intercalating with DNA. Placement of the dye in the reaction chamber enables immediate detection of the resulting reaction product without the end user taking action. Depending on the fluorescent dye used, the wavelength of the light that causes the intercalating dye to fluoresce is different. Dyes used for marking give visible light. The fluorescent dye intercalating with DNA (for example, SYBR® GREEN, EVAGREEN™, PIKOGREEN®, Ethidium bromide, Calcein, Acridine Orange, Proflavin, Acriflavine and others) is used to detect the amplification reaction product.

For detection, according to the first and second aspect of the invention, the real-time detection of nucleic acid amplification product as well as the end-point technique oligonucleotides with a quantum dot molecule are attached at the 5' end and a quencher attached at the 3'end. The sequence of the oligonucleotides used is complementary to the portion of the amplified region of the deoxyribonucleic acid fragment located between the designed primers F1 and B1c and for the portion of the amplified region of the nucleic acid fragment located between the designed primers F1c and B1. During the amplification reaction, a polymerase having a strand displacement activity and 5'>3' exonuclease activity is used, e.g. Bst DNA Polymerase, Full Length.

During the deoxyribonucleic acid amplification reaction, the probe binds to the complementary fragment in the amplified DNA segment. During the amplicon elongation, due to the exonuclease properties of the polymerase, the attached oligonucleotide is degraded which results in separation of the quencher from the quantum dot. As a result of separation of the quencher from the quantum dot, electromagnetic radiation is emitted in the UV, IR or VIS range after excitation of the quantum dot with the radiation wavelength specific for the material from which the quantum dot was created. The emitted signal is registered by the photosensitive element.

The use of quantum dots causes a significant reduction in the detection threshold due to the possibility of using a source of excitation light with a higher power, thanks to which it is possible to register the emission of electromagnetic radiation coming from a much smaller amount of released quantum dots. In addition, the use of quantum dots for marking oligonucleotide fragments allows for a better separation of excitation wavelength from the wavelength of emission signal in which detection of electromagnetic radiation occurs. What is more, quantum dots have an increased bleaching durability compared to traditional fluorochromes, which facilitates detection throughout the entire amplification reaction.

In order to amplify the specific reaction product, the following isothermal amplification technologies may be used: Loop-mediated isothermal amplification (LAMP); Strand displacement amplification (SDA); Helicase-dependent amplification (HDA); Nicking enzyme amplification reaction (NEAR). Lyophilisate contains experimental amounts of deoxynucleotides (dNTPs); specific primer sequences, reaction buffer components, magnesium ions $Mg^{2+}$; polymerase capable of carrying out an amplification reaction; in some cases, reverse transcriptase and other components necessary to amplify the selected sequence of genetic material. A set of primers (at least a pair of primers) with a unique sequence specific for the genome of a given pathogen determines the specificity of the reaction. The water coming from the isolation chamber 7 together with the material dissolved therein is loaded into the reaction chamber 8.1, 8.2, 8.3, 8.4.

The amplification process of a selected nucleic acid fragment takes place in the reaction chamber 8.1, 8.2, 8.3 at a constant temperature of at least 40° C. for a minimum of 5 minutes. The specific primer sequences are binding to the template DNA (isolated in the pre-isolation chamber 7), derived from the various pathogens present in the biological material. If the biological material is RNA, the amplification process is preceded by reverse transcription using the so-called random primers, resulting in cDNA. Once specificity has been determined by the primer, the DNA polymerase synthesizes the complementary strand. During the LAMP process about 30 µg/µl of DNA is received. Such a large amount of double-stranded DNA is shown by the dyes intercalating with the genetic material. By adding a fluorescent dye to the lyophilisate, the combining of the dye with the DNA occurs simultaneously with its amplification during the reaction. Upon completion of the reaction, the reaction mixture is illuminated with a light of a specific wavelength which excites the dye intercalating with DNA on a fluorescence basis. Detection of the reaction product is achieved by registering the wavelength emitted by the dye and double-stranded DNA complex specific for the dye used, using the photosensitive element. The construction of the reaction cartridge 6 and the material from which it was made (i.e. transparent polymer), allows the transmission of the light both exciting the dye-DNA complex as well as the light emitted by this complex. The result is interpreted on the basis of the presence of light or its absence (positive result—current light, negative—no light).

EXAMPLE 2

In the present embodiment the device for detecting the genetic material in the bological sample comprises in general three main elements, i.e. measurement device (shown in the form of a block diagram in FIG. 5), the reaction cartridge 6 and the sampling system 1. FIG. 1 schematically shows a construction of one, non-limiting embodiment of the reaction cartridge 6 and sampling system 1. Connected sampling system 1 and the reaction chamber 6 are arranged in the measurement device which is designed to steer and control the whole process of genetic material analysis. The measurement device takes the form of a small mobile device, like a mobile phone, which contains a receptacle housing the reaction cartridge 6.

The sampling system 1 comprises a blood-collecting capillary 2 which is connected to the water chamber, which is a water tank closed with a diaphragm connected to the pressure-producing chamber. Such a system works as the first pump 1 producing pressure exerting water from the water chamber through a capillary 2 with a sampled biological material. Proper operation of the sampling system 1 provides the vent 3, which forms the branching of the capillary 2 and jointly controlled valves Z1 and Z2. During use, the sampling system 1 is in contact with liquid biological material (e.g. blood), where the capillary 2 is filled under the influence of capillary forces When filling the capillary 2 with biological material, the valve Z1 is open and the valve Z2 is closed to ensure proper operation of the system. After filling the capillary 2 with the biological material, the sampling system 1 is placed in the reaction cartridge 6. A tight and stable connection of these elements is provided by a matching plug 4 in the sampling system 1 and a receptacle 5 in the reaction cartridge 6. The connection of this plug 4 to the receptacle 5 provides a stable and sealed fluid connection between the sampling system 1 and the reaction cartridge 6. After placing the sampling system 1 in the reaction cartridge 6, the valve Z1 is closed, the valve Z2 is opened, and the activation of the first pump P1 (i.e. water tank closed with a diaphragm connected to the pressure-producing chamber). Activation of the first pump P1 occurs by mechanical compression of the chamber. The activation method of the first pump P1 is not limiting in this case, and any method known in the prior art may be used to transport of the liquid, e.g. heating with LEDs a substance with a high thermal expansion coefficient. This operation removes the biological material from the capillary 2 together water from the water chamber. The mixture of water and biological material is transported through a suitable channel to the isolation chamber 7. In the isolation chamber 7 there is a material capable of binding the inhibitors of amplification reaction of the genetic material, and the isolation chamber 7 has access to the water chamber. Collected biological material is provided into this isolation chamber 7. The capacity of this isolation chamber is about 100 µl. There is a connecting channel with a hollow chamber closed with a diaphragm connected to a pressure-producing chamber forming a second pressure-generating pump P2, extending from the isolation chamber 7. The isolation chamber 7 is connected to the second pump P2 by a reflective infra-red liquid detector D1 and a normally open valve Z3. The second P2 pump in turn is connected by a normally open valve Z4 with a vent 9 located at the end of the reaction cartridge 6, opposite to the receptacle 5. This configuration of the valves Z3 and Z4 allows the mixture of biological material and water to be introduced through the isolation chamber 7 further towards the second pump P2. When the test mixtures reach the liquid detector D1, the isolation chamber 7 signals its filling and the Z11 and Z3 valves are closed. Then, the biological material in the isolation chamber 7 is heated to a suitable temperature for a specified time period, which causes the release of the genetic material encapsulated in the cells/protein envelope.

After the stage of isolating the genetic material from the collected sample is completed, the valves Z3, Z5, Z6 and Z7 are opened and the second pump P2 is activated. The valves Z5, Z6 and Z7 are located on separate channels connecting the isolation chamber 7 to the corresponding reaction chambers 8.1, 8.2, 8.3. Each reaction chamber 8.1, 8.2, 8.3 is in turn connected with a corresponding vent 9 located on the edge of the reaction cartridge 6, via liquid detectors D1, D2, D3, respectively, and normally open valves Z8, Z9, Z10, respectively. Activation of the second P2 pump, along with the configuration of the valves Z5, Z6, Z7 and Z8, Z9, Z10 allows the isolated genetic material to be moved into the reaction chambers 8.1, 8.2, 8.3. After receiving the signal from the D1, D2, D3 liquid detectors the valves Z8, Z9, Z10 are closed. Then, the valves Z5, Z6 and Z7 are closed next. In this way, the reaction chambers 8.1, 8.2, 8.3 are filled with the isolated genetic material. The reaction chambers 8.1, 8.2, 8.3 contain lyophilized reagents in their volume, containing all the necessary ingredients for the amplification of the genetic material. The master mix in the reaction chambers 8.1, 8.2, 8.3, 8.4 also comprises a lyophilized fluorescent dye intercalating with genetic material. The capacity of the reaction chambers 8.1, 8.2, 8.3 is in the range of 20 µl to 25 µl. In the present embodiment three reaction chambers 8.1, 8.2, 8.3 are provided, including a test chamber 8.1 comprising specific primers for the genetic material tested, a positive control chamber 8.2 that contains primers specific to a particular portion of the genetic material from which the biological material sample is derived and a negative control chamber 8.3 that does not contain primers, but other reaction components. The positive control chamber 8.2 is designed to allow for control of the polymerase, temperature conditions and the isolation of the genetic material. The negative control chamber 8.3 allows to control the lyophilization process (e.g. sterility) and control of the valve behaviour, which could cause mixing of the contents of these reaction chambers. Of course, the number of chambers used is not a limitation of the present invention, and the person skilled in the art will, for example, use a increase in the number of chambers 8.1, 8.2, 8.3 for the simultaneous analysis of different pathogens.

To amplify the genetic material, the reaction chambers 8.1, 8.2, 8.3 are then heated to the appropriate temperatures. Simultaneously with the amplification (or subsequently) the fluorescence signal detected from the fluorescent tag used is attached to the amplified genetic material. Signal increase is equal to the increase in light intensity generated by the fluorescent tag used.

After the whole process and reading the result by the optical system with the camera 28, the regions containing the biological material are heated with UV LEDs 29 emitting radiation at wavelengths ranging from 350 nm to 450 nm (or laser) to 150° C. for 2 to 3 second to neutralize biological hazard. At lower UV power, these UV LEDs 29 simultaneously serve to excite fluorescence (illuminate reaction cartridge 6). UV exposure results in the destruction of biological material and depolymerization of the reaction chamber material 6, which reduces the biological hazard and disintegrates the polymer, favourably protecting the environment and ensuring proper disposal.

Throughout the process of biological material analysis, the thermal treatment of the liquid biological material is carried out in the isolation chamber 7 and in the reaction chambers 8.1, 8.2, 8.3. The energy required to heat the isolation chamber 7 and the reaction chambers 8.1, 8.2, 8.3 is communicated without contact. The source of energy is light emitting diodes (LEDs), which emit light radiation in the UV-VIS range. For example, wavelengths emitted by LEDs can be selected from 350 nm to 500 nm. The LEDs are located inside the measurement device and are arranged to illuminate the area of the isolation chamber 7 and the reaction chambers 8.1, 8.2, 8.3. By using a transparent material for the construction of the reaction cartridge 6, which is characterized by high light transmission, it is possible to use an energy-efficient heating method for the respective chambers. The temperature of the reaction chamber 8.1, 8.2, 8.3 and isolation chamber 7 is controlled with no contact by a pyrometer with a digital processing block. The entire system is controlled by a microprocessor driver with built-in software. Furthermore, the low-power UV LED is used in the measuring device to illuminate the inside of the reactor, which is necessary for image recording by the CCD. Detection of the biochemical reaction product is based on determining the quantized levels of signals from the CCD detector RGB channels. The design of the device allows for continuous recording of colour signals. Using the illuminating diode allows continuous recording of the image by the detector, as it is not necessary to constantly illuminate the sample with an external light source.

Figure 5:
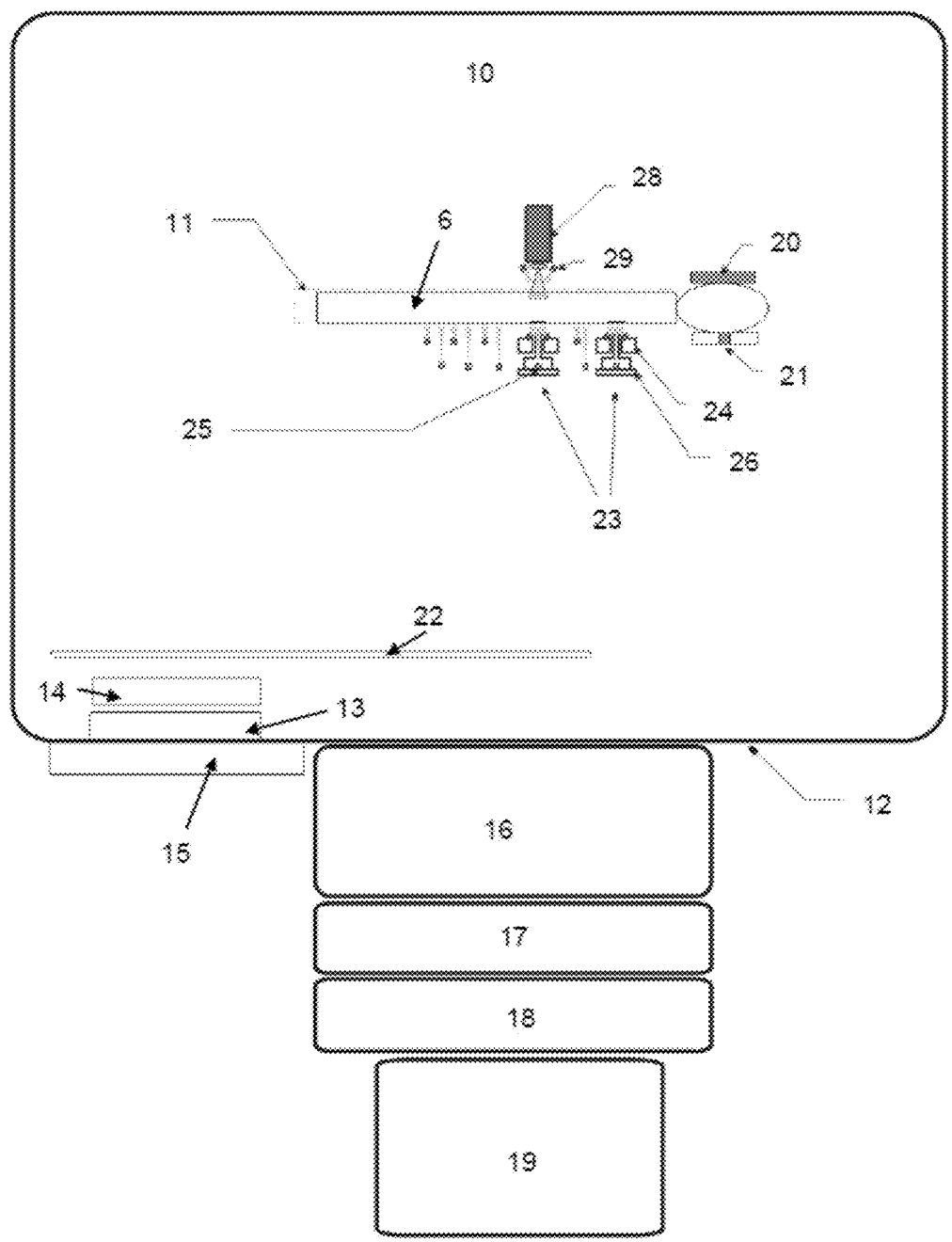
FIG. 5 shows a block diagram of the measurement device according to one embodiment of the present invention.

Construction of the measurement device according to one embodiment of the present invention is shown in block diagram form in FIG. 5. In general, a measurement chamber 10 is constructed so that it houses a reaction cartridge 6 is located in the measurement device. In order to properly locate the reaction cartridge 6 in the measurement chamber 10, a positioning mechanism 11 for the reaction cartridge 6 is provided. The measurement chamber 10 is a closed structure that is covered by an outside thermal insulation 12, which facilitates keeping the set temperature inside. Maintaining the isothermally controlled temperature inside the measurement chamber 10 (e.g. in the range of 4° C. to 40° C.) ensures the correct heating environment 13 (e.g. in the form of a Peltier assembly). In order to properly distribute the heated air inside the measurement chamber 11, a fan 14 and an air-mixing wheel 22 are used. The efficiency of the heating system 13 is ensured also by the radiator 15 located outside the measurement chamber 10. The measurement device also contains further blocks necessary for the proper functioning of the device, such as the image control and analysis module 16, the communication module 17, the power supply module 18, and the display 19. The functionality of the above-mentioned blocks and their construction are well known to those skilled in the art, so their exact description is omitted to simplify the discussion. The measurement chamber 20 of the measurement device also provides the pressure setting mechanism 10 for the purpose of activating the pump P1 in the reaction cartridge 6. A pressure sensor 21 is located opposite to control the set pressure on pump P1. In order to ensure a correct temperature in the isolation chamber 7 and the reaction chambers 8.1, 8.2, 8.3, a number of heating units 23 are provided in the measurement chamber 10 which are so positioned relative to the reaction cartridge 6 that the emitted light streams illuminate the isolation chamber 7 and the reaction chambers 8.1, 8.2, 8.3, 8.4, respectively. More specifically, each heating unit 23 consists of LEDs with radiators 24, a temperature detector 25, and a temperature detector stabilizer 26. Heating of the isolation chamber 7 and the reaction chamber 8.1, 8.2, 8.3 is performed with LEDs with a continuously adjustable photon energy stream ranging from 400 nm to 500 nm, which is preferred due to high photon emission performance and translates into high power reaching the absorption layer at the bottom of the isolation chamber 7 and reactor chambers 8.1, 8.2, 8.3. In order to compensate for the temperature of the bottom of the chamber 7, 8.1, 8.2, 8.3 and absorption of energy, to prevent degradation of the lyophilized biological material in chambers 8.1, 8.2, 8.3, the absorption layer completely absorbing photon energy was used. The layer is made of materials e.g. Cu or Al coated with oxides (in the present example $Al_2O_3$, dyed black) and other materials with good absorption properties and good thermal conductivity (including modified polymers e.g. carbon or graphene).

The temperature increase over time in chambers 7, 8.1, 8.2, 8.3 is achieved by increasing the power of the light stream and decrease through the isothermal measurement chamber 10 at a temperature from 4° C. to 40° C. With the constant thermal resistance of the isolation chamber 7 or reactor chamber 8.1, 8.2, 8.3 to the surroundings, the rate of the decreasing temperature can be controlled by change the ambient temperature of the reaction cartridge 6. Depending on the desired temperature decrease rate, the temperature inside the device (i.e. in the measurement chamber 10) is set and a suitable power is applied to the absorption layer of chambers 7, 8.1, 8.2, 8.3. In this way any temperature profile can be obtained in the range from 25° C. to 100° C. with high increase and decrease rates. The absorption layer of the chambers has a high thermal conductivity which eliminates the possible heterogeneity of the light stream from the LEDs and ensures no temperature gradients in the area of the working chambers.

Because the temperature measurement is done by a temperature detector such as a pyrometer with a built-in radiation permeable filter in the range of 8 μm to 12 μm, it is possible to simultaneously measure the temperature and supply energy to the isolation chambers 7 and reaction chambers 8.1, 8.2, 8.3. In this case there are no periods of lack of control over the temperature control in the isolation chambers 7 and reaction chambers 8.1, 8.2, 8.3

In addition, a series of LEDs 27, analogically arranged so that the beam of light generated, illuminates the device, is provided to operate the Z1-Z11 valves and D1-D4 liquid detectors. The optical system with the camera 28 which may have the form of a CCD detector and is intended to detect the light signal resulting from fluorescent dyes resulting from reaction in the reaction chamber 8.1, 8.2, 8.3. In order to allow this UV LEDs 29 are also provided, which illuminate the detection area.

EXAMPLE 3

Figure 2:
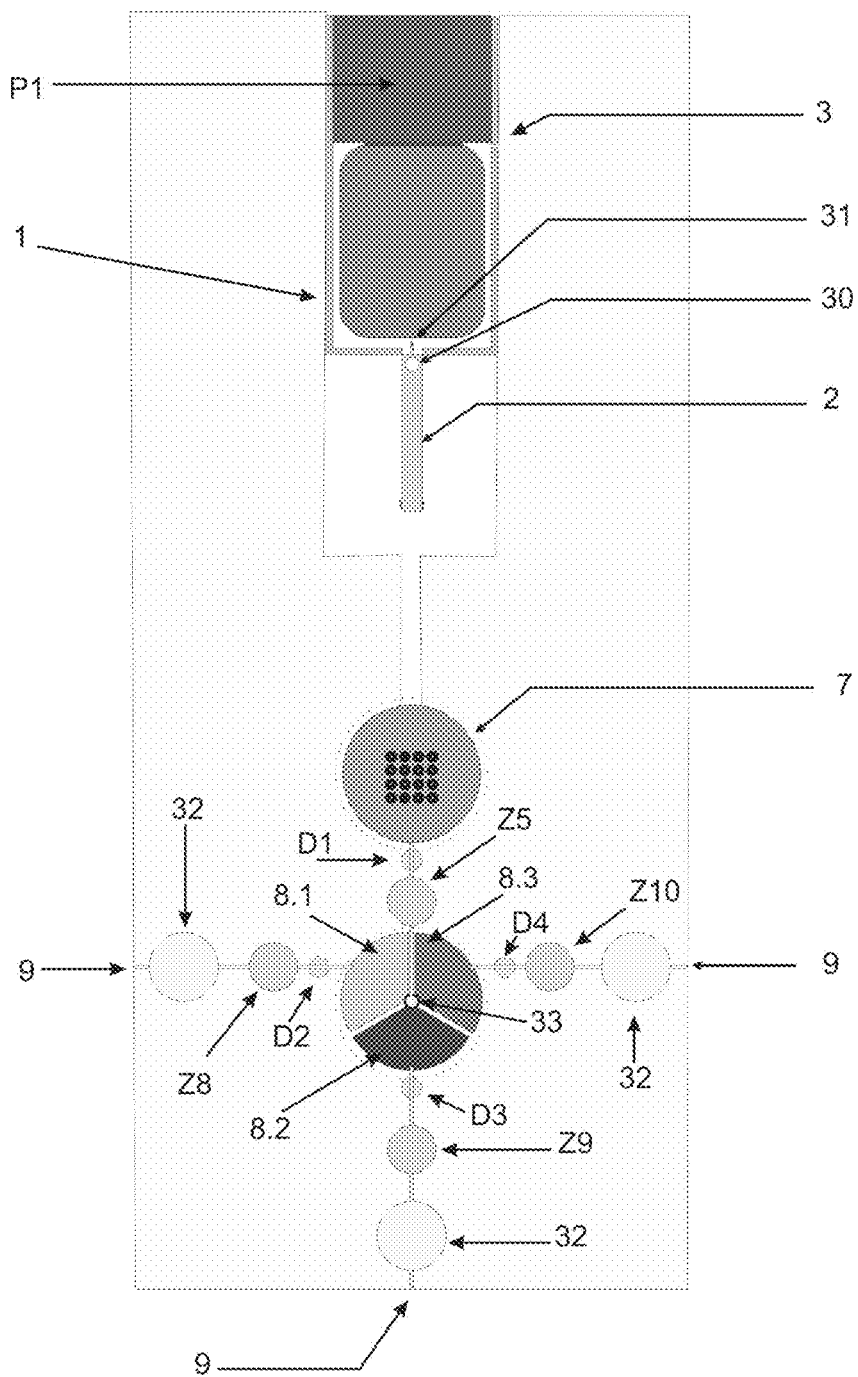
FIG. 2 shows the reaction cartridge according to another embodiment of the present invention.
Figure 4:
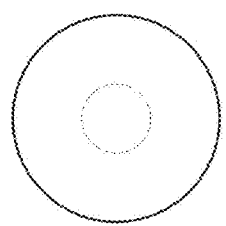
FIG. 4 shows various embodiments of the valves used in different embodiments of the reaction cartridge.
Figure 4:
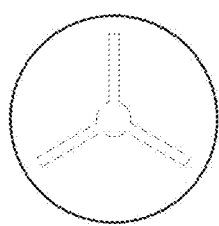
Figure 4:
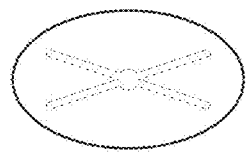
Figure 4:

FIG. 2 schematically shows another embodiment of reaction cartridge 6 used in the device for detecting genetic material in a biological sample according to the present invention. The general design and principle of operation of the reaction cartridge 6 shown in the present embodiment is consistent with the construction and principle of operation of the reaction cartridge 6 of Example 1. The fundamental difference between the comparative reaction cartridges 6 is that in the reaction cartridge 6 from example 2 integral sampling system 1 is used (it is not a separate device as in the first embodiment of the present invention). The reaction cartridge 6 is therefore a compact structure, devoid of detachable elements. In this case, the collected biological material is introduced into the sampling system 1, which forms an integral part of the reaction cartridge 6. Also in this example, the capillary 2 can be distinguished, which by means of the capillary forces absorbs the biological material. At the other end of the capillary 2 a control window 30 is provided which signals the filling of the capillary 2 with the biological material. In the present embodiment the first pump P1 is made by means of mechanical elements such as piston and bellows. In this embodiment It should be emphasized that water for the reaction chamber 6 is provided in the form of capsules, which allows for easy sterilization and the possibility of separating the wet process in the production of the reaction chambers 6. Water release takes place just before the test and is performed by needle injection 31 when the pump P1 starts operating. Transport of the biological material and the products from the isolation chamber 7 to the reaction chambers 8.1, 8.2, 8.3, 8.4 is provided by pump P1 by extruding water from the capsule. This simplifies the process control on the device. Suitable pressure during heating is provided by the pressure sensor 21 in the measurement device and the corresponding control of the valves Z5, Z8, Z9, Z10. In this embodiment, the construction of reaction chambers 8.1, 8.2, 8.3 also deserves mentioning. Each of the reaction chambers 8.1, 8.2, 8.3, 8.4 in a top view are complementary circles. The reaction chambers 8.1, 8.2, 8.3 complement each other to form a circular region comprising all the reaction chambers 8.1, 8.2, 8.3, connected in the middle by means of a valve or diaphragm 33. In this embodiment, various valve designs 33 may be used that do not affect the scope of the embodiment. Exemplary valves 33, usable in reaction cartridges 6, are shown in FIG. 4 A-D, hydrophobic circular valve, hydrophobic—mechanical round valve, hydrophobic—mechanical elliptic valve, hydrophobic—mechanical rectangular valve, respectively. The presented mechanical valves act on the deformation of the flexible material from which the valve was made. A specific force is required, which at the same time defines the pressure, which having been exceeded causes the liquid to flow in a given direction. The shape of the valve is such that in the second direction the elastic deformation is blocked, thus blocking the flow of liquid for that direction. The hydrophobic valves operate on the principle that the liquid must overcome the surface tension forces in contact with the hydrophobic valve material (while the air flows freely). This allows to block the flow of the liquid in the channel to a predetermined pressure depending on the diameter of the opening in the valve and the hydrophobicity of the material from which the valve is made. In the case of simultaneous filling of the three channels with the liquid, after placing the hydrophobic valves at the ends of the channels they will be automatically filled. The air will flow unobstructed, and the liquid will stop successively on these valves, because more pressure will be required to for the liquid to flow through the valves. The combination of these two types of valves makes it easy to control the flow of liquid in the reaction cartridge 6.

Moreover, in the present embodiment no additional pump P2 is used and substantially the number of valves used was reduced (compared to the reaction cartridge 6 of the first embodiment). In addition, due to the construction of the reaction chambers 8.1, 8.2, 8.3, the outlet channels are directed towards the three different edges of the reaction cartridge 6 and compensation chambers 33 are provided prior to the vent 9 to prevent the liquid from exiting the reaction cartridge 6 into the measurement device.

The other components and the principle of operation of the reaction cartridge 6 coincide with those disclosed in the first embodiment of the reaction cartridge 6.

EXAMPLE 4

Figure 3:
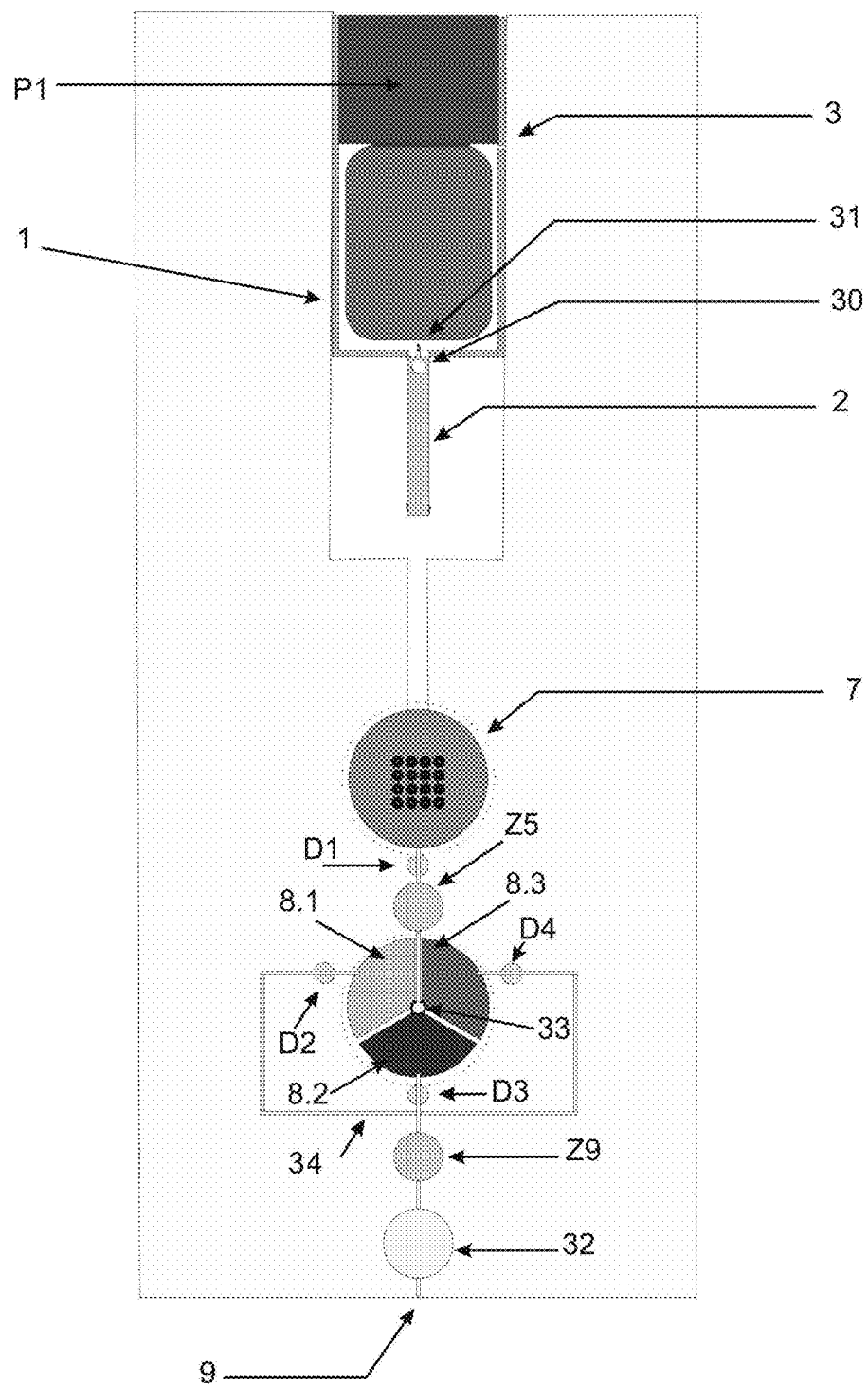
FIG. 3 shows the reaction cartridge according to yet another embodiment of the present invention.

The reaction cartridge 6 shown in FIG. 3, being yet another embodiment of the present invention, differs from the reaction cartridge 6 shown in FIG. 2 only in that in each reaction chamber 8.1, 8.2, 8.3 two valves 33 are used at the inlet and outlet of the reaction chamber 8.1, 8.2, 8.3) and a connecting channel 34 which is intended to provide a stable and controlled liquid flow in one direction with pressure variations caused by heating the reaction chambers 8.1, 8.2, 8.3. In the solution presented in the present embodiment, in contrast to the solution presented in the second embodiment, there are no Z8 and Z10 valves, which greatly simplifies the design of the reaction cartridge 6 and its operation. The connecting channel 34 serves to vent the reaction chambers 8.1, 8.2, 8.3. Due to the fact that the valves prevent the retraction of the liquid, there is no uncontrolled mixing of the liquid in the reaction chambers 8.1, 8.2, 8.3. Placing two valves in the reaction chambers 8.1, 8.2, 8.3 allows the use of only one valve normally open at the outlet to ensure proper operation of the system.

EXAMPLE 5

Detection of HIV in the blood using the method of the present invention and the device of the present invention.

To analyse the presence of HIV virus in a sample taken from a patient, a method and device for the detection of genetic material in a biological sample according to the present invention, described in detail in Examples 1 and 2. In isolation chamber 7 Chelex 100 is used. DNA isolation involves the thermal degradation of the cell membrane or viral protein envelope and the release of genetic material that is encapsulated in the viral cells/protein envelope. Chelex 100 is necessary to catch inhibitors that can block the polymerase and produce false negative results. Chelex 100 is prepared as a 5% mixture in deionized water, nuclease-free, it can also be immobilized at the bottom of the isolation chamber in the form of a porous layer. To perform isolation in the isolation chamber, the blood is heated at 95° C. for 5-10 min.

Lyophilized reagents, including buffer, dNTPs, MgSO4, Primer Mixer, Bst 3.0 polymerase, SYBR® GREEN are in the reaction chambers. The amplification of genetic material is carried out in reaction chambers 8.1, 8.2, 8.3 by heating at 65° C. for 30 min. There are specific HIV primers in the test chamber 8.1. In the endogenous positive control chamber 8.2 there are specific primers for the human gene. In the negative control chamber 8.3 there are no primers added, but it contains the other components of the reaction. LAMP reaction and detection—takes place in the reaction chambers 8.1, 8.2, 8.3 and consists in amplifying genetic material of a given pathogen (and human genetic material for endogenous control) using the Bst 3.0 polymerase enzyme. Specific primers added to the reaction are binding to selected fragments of the tested genome and determine the fragment amplified in the reaction. At the end of the reaction, approximately 10-50 μg/μl of the amplified DNA fragment is formed. SYBR® GREEN present in the reaction mixture is combined with the reaction product and, when combined with double-stranded DNA, becomes fluorescent (illuminates when light is of the correct wavelength). Product increase is equal to the increase in light from the dye. At the end of the reaction, when the result is positive and the tested fragment is amplified light is visible, when the result is negative there is no light. Other reaction components (buffer, MgSO4, dNTPs) are added to provide suitable working conditions for Bst 3.0 polymerase.

In the process of isolating the DNA/RNA material in the reaction chamber, the pathogen is neutralized. The only danger can be the residue of the genetic material in the capillary 2 or channels in the reaction cartridge 6. Thus, after the detection, the residue of the genetic material is recycled, which is performed by exposing the reaction cartridge 6 (in particular the isolation chamber 7 and the reaction chambers 8.1, 8.2, 8.3) to UV radiation to heat the individual components to a temperature above 100° C. and thereby dispose of genetic material. This allows to safely dispose of used reaction cartridge 6 without having to carry out complicated disposal procedures.

The invention claimed is:

1. A method of detecting genetic material in a biological sample comprising of:
   a) loading the biological sample into a reaction cartridge and placing the reaction cartridge in a measurement device,
   b) moving the biological sample to an isolation chamber,
   c) isolating genetic material from the sample by heating the isolation chamber,
   d) moving the isolated genetic material into a plurality of reaction chambers,
   e) amplifying the genetic material by heating the reaction chambers, and
   f) detecting the amplified genetic material by measuring a signal from a fluorescent dye;
   wherein heating of the isolation chamber and/or the plurality of reaction chambers is performed through a plurality of heating units of LEDs with temperature sensors.

2. The method according to claim 1, wherein at least one of the plurality of reaction chambers comprises freeze-dried reagents for amplification of genetic material and a fluorescent dye which binds to genetic material, and wherein simultaneously with the stage of amplification of genetic material a fluorescent signal from the fluorescent dye is registered.

3. The method according to claim 1, wherein at least one of the plurality of reaction chambers comprises freeze-dried reagents for amplification of genetic material, primers, and a quencher, and wherein simultaneously with the stage of amplification of genetic material a fluorescent signal from the fluorescent dye is registered.

4. The method according to claim 1 characterized in that a biological sample is taken from a sampling system and stage a) is performed by loading the sampling system into to the reaction cartridge.

5. The method according to claim 1, wherein the biological sample is moved to the isolation chamber via a capillary by applying capillary forces.

6. The method according to claim 1, wherein the plurality of reaction chambers comprises first, second and third reaction chambers, wherein the first reaction chamber is a test chamber including specific primers for the genetic material tested, the second reaction chamber is a positive control chamber that contains primers specific to a particular portion of the genetic material from which the biological material sample is derived, and the third reaction chamber is a negative control chamber containing reaction components without primers.

7. The method according to claim 6, wherein the first, second, and third reaction chambers are interconnected with a valve or a diaphragm.

8. A device for detecting genetic material in a biological sample comprising a reaction cartridge and measurement device, the measurement device comprising a measurement chamber having a receptacle housing the reaction cartridge, wherein the reaction cartridge comprises an isolation chamber for isolating genetic material, which is connected through channels with a plurality of reactions chambers for amplifying isolated genetic material, wherein at least one of the plurality of reaction chambers comprises a fluorescent dye for detecting amplified genetic material and other freeze-dried reagents for amplification of genetic material to be detected;
   wherein the measurement device comprises a plurality of heating units of LEDs with optical temperature detectors for heating the plurality of reaction chambers.

9. The device according claim 8 wherein the fluorescent dye for detecting amplified genetic material is a fluorescent dye which binds to genetic material.

10. The device according to claim 8, characterized in that the device comprises a detachable sampling system comprising a plug and a reaction cartridge comprising a receptacle fitted to said plug and providing a stable and tight fluid connection between the sampling system and the reaction cartridge; a measurement module for image control and analysis; a communication module; a power supply module; and a display module.

11. The device according to claim 10, wherein the sampling system comprises a capillary to which a biological sample is taken, connected with a first pump.

12. The device according to claim 10, wherein the reaction cartridge comprises first, second and third reaction chambers, wherein the first chamber is a test chamber including specific primers for the genetic material tested, the second chamber is a positive control chamber that contains primers specific to a particular portion of the genetic material from which the biological material sample is derived and the third chamber is a negative control chamber, containing reaction components without primers, wherein the reaction cartridge comprises a second pump.

13. The device according to claim 12, wherein a channel connects the isolation chamber with the second pump and the channel comprises a liquid detector.

14. The device according to claim 8, wherein the measurement chamber is insulated with thermal insulation.

15. The device according to claim 14, further comprising UV LEDs illuminating the detection area.

16. The device according to claim 8, further comprising additional LEDs for operating liquid detectors and valves; wherein at the bottom of the isolation chamber and/or the bottom of at least one of the reaction chambers there is an absorption layer absorbing photon energy.

* * * * *